(12) United States Patent
Habeck et al.

(10) Patent No.: US 6,413,503 B1
(45) Date of Patent: Jul. 2, 2002

(54) USE OF CYCLIC ENAMINES AS LIGHT PROTECTION AGENTS

(75) Inventors: Thorsten Habeck, Meckenheim; Frank Prechtl, Frankfurt; Thomas Wünsch, Speyer; Horst Westenfelder, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/583,288

(22) Filed: May 31, 2000

(30) Foreign Application Priority Data

Jun. 18, 1999 (DE) .......................... 199 28 033

(51) Int. Cl.$^7$ .............................. A61K 7/42; A61K 7/44; A61K 7/00

(52) U.S. Cl. .......................... 424/59; 424/60; 424/400; 424/401

(58) Field of Search ............................ 424/59, 60, 400, 424/401

(56) References Cited

U.S. PATENT DOCUMENTS

| | | | |
|---|---|---|---|
| 4,387,089 A | 6/1983 | DePolo | 424/59 |
| 4,950,467 A | 8/1990 | Phalangas et al. | 424/59 |
| 5,576,354 A | 11/1996 | Deflandre et al. | 514/685 |
| 5,587,150 A | 12/1996 | Deflandre et al. | 424/59 |

FOREIGN PATENT DOCUMENTS

| | | |
|---|---|---|
| EP | 351 398 | 1/1988 |
| EP | 514 491 | 11/1992 |
| FR | 2 440 933 | 6/1980 |
| WO | WO 91/11989 | 8/1991 |

*Primary Examiner*—Shelley A. Dodson
(74) *Attorney, Agent, or Firm*—Keil & Weinkauf

(57) ABSTRACT

The use of compounds of the formula I

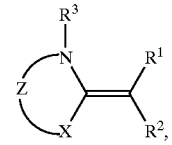

in which

R$^1$ and R$^2$ are identical or different, electron-withdrawing radicals chosen from the group consisting of cyano, alkyl- or arylcarbonyl, alkyloxy- or aryloxycarbonyl and optionally substituted aminocarbonyl, R$^3$ is a hydrogen atom, a C$_1$–C$_{20}$-alkyl radical or a C$_3$–C$_{20}$-cycloalkyl radical or a radical of the formula —CH$_2$—CH$_2$—SO$_3$—M$^+$, where M$^+$ is a cation, X is the divalent radical of oxygen, sulfur or the radical

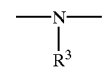

where R$^3$ is as defined above, Z is the divalent radical of the formula II or III, which forms a fused system with the radical of the formula I

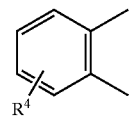

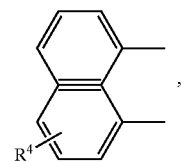

where R$^4$ can be bonded one or more times to the benzylidene ring I or naphthylidene ring II, and is hydrogen, alkyl, cycloalkyl, alkyloxy, cycloalkyloxy, alkoxycarbonyl, mono- or dialkylaminocarbonyl, alkylamino, dialkylamino, each having up to 20 carbon atoms, and also cyano, amino and SO$_3$—M$^+$, where M$^+$ is a cation, as photostable UV filters in cosmetic and pharmaceutical preparations to protect human skin and human hair against solar rays, alone or together with compounds which absorb in the UV region and are known per se for cosmetic and pharmaceutical preparations.

8 Claims, No Drawings

USE OF CYCLIC ENAMINES AS LIGHT PROTECTION AGENTS

The invention relates to the use of bicyclic and tricyclic enamines which carry electron-withdrawing substituents on the-ene double bond as light protection agents in cosmetic and pharmaceutical preparations and as light protection additives (light stabilizers) in plastics. The invention further relates to novel compounds of said type which have a light protection action.

The light protection agents used in cosmetic and pharmaceutical preparations have the task of preventing, or at least diminishing the consequences of, harmful effects of sunlight on the human skin. However, these light protection agents also serve to protect other ingredients from decomposition or breakdown by UV radiation. In hair cosmetic formulations, the aim is to reduce damage to the keratin fibers by UV rays.

The sunlight reaching the surface of the earth contains UV-B radiation (280 to 320 nm) and UV-A radiation (>320 nm), which are directly adjacent to the visible light region. The effect on the human skin is manifested, particularly in the case of UV-B radiation, by sunburn. Accordingly, the industry offers a relatively large number of substances which absorb UV-B radiation and thus prevent sunburn.

Dermatological investigations have now shown that UV-A radiation is also perfectly capable of causing skin damage and allergies by, for example, damaging the keratin or elastin. This reduces the elasticity and water storage capacity of the skin, i.e. the skin becomes less supple and tends to form wrinkles. The noticeably high incidence of skin cancers in areas of strong solar radiation shows that damage to the genetic information in the cells is evidently also caused by sunlight, specifically by UV-A radiation. All these findings would therefore suggest that it is necessary to develop efficient filter substances for the UV-A region.

There is a growing demand for light protection agents for cosmetic and pharmaceutical preparations which can be used in particular as UV-A filters and whose absorption maxima ought therefore to be in the range from about 320 to 380 nm. In order to achieve the desired effect using the minimum amount, light protection agents of this type should additionally have a high specific absorbance. Light protection agents for cosmetic preparations must also meet a large number of other requirements, for example good solubility in cosmetic oils, high stability of the emulsions prepared therewith, toxicological acceptability and low intrinsic odor and low intrinsic color.

Another requirement which light protection agents must meet is adequate photostability. However, this requirement is met only inadequately, if at all, by the UV-A-absorbing light protection agents available hitherto.

French Patent No. 2 440 933 describes 4-(1,1-dimethylethyl)-4'-methoxydibenzoylmethane as a UV-A filter. It is proposed to combine this particular UV-A filter, which is sold by GIVAUDAN under the name "PARSOL 1789", with various UV-B filters in order to absorb all UV rays having a wavelength from 280 to 380 nm.

However, this UV-A filter does not have sufficient photochemical stability, when used alone or in combination with UV-B filters, to ensure sustained protection of the skin during sunbathing for extended periods, which means that repeated applications at regular and short intervals are required if effective protection of the skin from all UV rays is desired.

For this reason, EP-A-0 514 491 discloses the stabilization of the insufficiently photostable UV-A filters by adding 2-cyano-3,3-diphenylacrylic esters, which themselves act as filters in the UV-B region.

Furthermore, it has already been proposed in EP-A-0 251 398 to combine chromophores which absorb UV-A radiation and UV-B radiation into a molecule via a linker. This has the disadvantage that firstly it is no longer possible to freely combine UV-A and UV-B filters in the cosmetic preparation, and that difficulties in the chemical linkage of the chromophores permit only certain combinations.

U.S. Pat. No. 4,950,467 describes the use of 2,4-pentadienoic acid derivatives as UV absorbers in cosmetic preparations. The monoaryl-substituted compounds specified in this patent specification as being preferable likewise have the disadvantage that their photostability is insufficient.

It is an object of the present invention to propose light protection agents for cosmetic and pharmaceutical purposes which absorb predominantly in the UV-A region (and optionally alternatively in the UV-B region) with high absorbance, are photostable, have low intrinsic color, i.e. a sharp band structure, and are soluble in oil or water depending on the substituent.

We have found that this object is achieved according to the invention by the use of compounds of the formula I

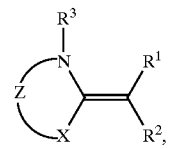

in which
R$^1$ and R$^2$ are identical or different, electron-withdrawing radicals chosen from the group consisting of cyano, alkyl- or arylcarbonyl, alkyloxy- or aryloxycarbonyl and optionally substituted aminocarbonyl,
R$^3$ is a hydrogen atom, a C$_1$–C$_{20}$-alkyl radical or a C$_3$–C$_{20}$-cycloalkyl radical or a radical of the formula —CH$_2$—CH$_2$—SO$_3$—M$^+$, where M$^+$ is a cation,
X is the divalent radical of oxygen, sulfur or the radical

where R$^3$ is as defined above,
Z is the divalent radical of the formula II or III, which forms a fused system with the radical of the formula I

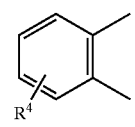

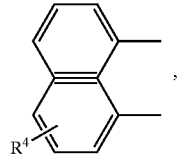

where R$^4$ can be bonded one or more times to the benzylidene ring I or naphthylidene ring II, and is hydrogen, alkyl, cycloalkyl, alkyloxy, cycloalkyloxy, alkoxycarbonyl, mono- or dialkylaminocarbonyl, alkylamino, dialkylamino, each having up to 20 carbon atoms, and also cyano, amino and $SO_3$—$M^+$, where $M^+$ is a metal cation, as photostable UV filters in cosmetic and pharmaceutical preparations to protect human skin and human hair against solar rays, alone or together with compounds which absorb in the UV region and are known per se for cosmetic and pharmaceutical preparations.

Preferred compounds are those in which Z is the radical of the formula II.

With regard to the substituents, preference is given to compounds in which $R^1$ is cyano or alkyloxycarbonyl having from 2 to 12 carbon atoms, $R^2$ is hydrogen, $R^3$ is hydrogen or methyl, and $R^4$ is $C_1$–$C_8$-alkyl, $C_1$–$C_8$-alkoxy or $SO_3$—$M^+$, where $M^+$ is a cation chosen from the group consisting of

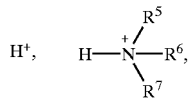

where $R^5$, $R^6$ and $R^7$ are hydrogen or low molecular weight alkyl or hydroxyalkyl, and metal cations.

The alkyl radicals in the substituents $R^1$ to $R^4$ preferably have from 1 to 8 carbon atoms and are, in particular, low molecular weight alkyl radicals having from 1 to 5 carbon atoms and, preferably, methyl radicals.

The alkyl radicals in the substituents $R^4$ are isocyclic or heterocyclic radicals having from 5 to 10 ring atoms and from 3 to 5 carbon atoms which can be further substituted.

In the radicals —$SO_3$—$M^+$ and —$CH_2$—$CH_2$—$SO_3$—$M^+$, $M^+$ is usually an alkali metal, alkaline earth metal or ammonium cation, in particular $Na^+$, $K^+$, $NH_4^+$, $^+NH(C_2H_5)_3$ and $^+NH(—CH_2—CH_2OH)_3$. Generally speaking, only cations which are physiologically compatible at the use concentrations are suitable.

Of the compounds of the formula I, the compounds of the formula IV are novel

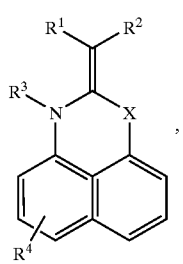

IV in which $R^1$, $R^2$, $R^3$ and $R^4$ are as defined above.

Equally novel are the compounds of the formula V

V

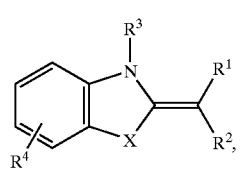

which X is the divalent radical of oxygen, sulfur or the radical

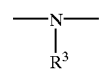

and $R^1$ and $R^2$ independently of one another are CN or alkoxycarbonyl having from 2 to 10 carbon atoms which can be substituted by a radical —$(CH_2)_n$—$SO_3$—$M^+$, $R^3$ is hydrogen, methyl or —$(CH_2)_n$—$SO_3$—$M^+$, and $R^4$ is hydrogen or one or more identical or different radicals $C_1$- to $C_8$-alkyl, $C_1$- to $C_8$-alkoxy or the radical —$SO_3$—$M^+$, where in each case n is the number 2 or 3 and $M^+$ is a cation chosen from the group consisting of

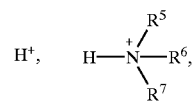

in which $R^5$, $R^6$ and $R^7$ are hydrogen or low molecular weight alkyl or hydroxyalkyl, and metal cations, with the proviso that the compound of the formula V has at least one radical —$(CH_2)_nSO_3$—$M^+$ or —$SO_3$—$M^+$.

The compounds of the formula I are obtained in a manner known per se, as is described, for example, in CH 601984, by reacting a compound of the formula VI

VI

compound of the formula VII

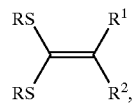

in which $R^1$ to $R^3$ are as defined above, and R is a low molecular weight alkyl radical, preferably methyl.

Using the compound

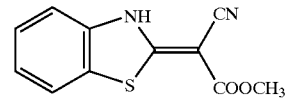

as an example, this may be exemplified by the following reaction equation.

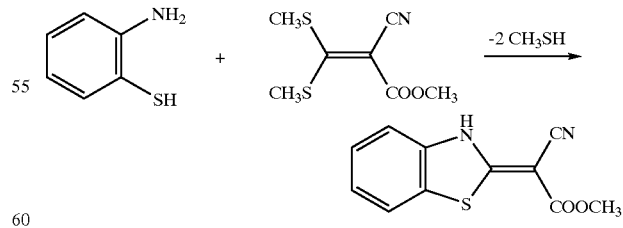

The reaction is carried out by heating to relatively high temperatures, e.g. to from 20 to 150° C., preferably from 50 to 120° C. and in particular from 70 to 100° C.

The present invention further relates to cosmetic and pharmaceutical preparations which comprise from 0.1 to 10% by weight, preferably from 1 to 7% by weight, based on the total amount of the cosmetic and pharmaceutical preparation, of one or more of the compounds of the formula I together with compounds which absorb in the UV-A and UV-B region and are known per se for cosmetic and pharmaceutical preparations as light protection agents, where the compounds of the formula I are generally used in a lesser amount than the UV-B-absorbing compounds.

The cosmetic and pharmaceutical preparations which comprise light protection agents are usually based on a carrier which comprises at least one oil phase. However, preparations merely based on water are also possible if compounds with hydrophilic substituents are used. Accordingly, suitable preparations are oils, oil-in-water and water-in-oil emulsions, creams and pastes, lipcare stick compositions or grease-free gels.

Sunscreen preparations of this type can, accordingly, be in liquid, paste or solid form, for example as water-in-oil creams, oil-in-water creams and lotions, aerosol foam creams, gels, oils, wax pencils, powders, sprays or alcoholic-aqueous lotions.

Other suitable emulsions are, inter alia, O/W macroemulsions, O/W microemulsions or O/W/O emulsions with compounds of the formula I in dispersed form, where the emulsions are obtainable by phase inversion technology, as in DE-A-197 26 121.

Customary cosmetic auxiliaries which may be suitable as additives are, for example, coemulsifiers, fats and waxes, stabilizers, thickeners, biogenic active ingredients, film formers, fragrances, dyes, pearlizing agents, preservatives, pigments, electrolytes (e.g. magnesium sulfate) and pH regulators. Suitable coemulsifiers are preferably known W/O and also O/W emulsifiers such as, for example, polyglycerol esters, sorbitan esters or partially esterified glycerides. Typical examples of fats are glycerides; waxes which may be mentioned are, inter alia, beeswax, paraffin wax or microwaxes, possibly in combination with hydrophilic waxes. Stabilizers which can be used are metal salts of fatty acids such as, for example, magnesium, aluminum and/or zinc stearate. Suitable thickeners are, for example, crosslinked polyacrylic acids and derivatives thereof, polysaccharides, in particular xanthan gum, guar guar, agar agar, alginates and tyloses, carboxylmethylcellulose and hydroxyethylcellulose and also fatty alcohols, monoglycerides and fatty acids, polyacrylates, polyvinyl alcohol and polyvinylpyrrolidone. Examples of biogenic active ingredients Are plant extracts, protein hydrolysates and vitamin complexes. Examples of customary film formers are hydrocolloids such as chitosan, microcrystalline chitosan or quaternized chitosan, polyvinylpyrrolidone, vinylpyrrolidone-vinyl acetate copolymers, polymers of the acrylic acid series, quaternary cellulose derivatives and similar compounds. Examples of suitable preservatives are formaldehyde solution, p-hydroxybenzoate or sorbic acid. Examples of pearlizing agents are glycol distearic esters such as ethylene glycol distearate, but also fatty acids and fatty acid monoglycol esters. Dyes which can be used are the substances suitable and approved for cosmetic purposes, as listed, for example, in the publication "Kosmetische F ärbemittel" [Cosmetic Colorants] from the Farbstoffkommission der Deutschen Forschungsgemeinschaft, [Dyes Commission of the German Research Society], published in Verlag Chemie, Weinheim, 1984. These dyes are normally used in concentrations of from 0.001 to 0.1% by weight, based on the total mixture.

An additional content of antioxidants is generally preferred. Thus, favorable antioxidants which can be used are all antioxidants which are customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoides, carotenes (e.g. β-carotene, lycopene) and derivatives thereof, chloregenic and derivatives thereof, lipoic acid and derivatives thereof (e.g. dihydrolipoic acid), aurothioglucose, propylthiouracil and other thiols (e.g. thiorodoxin, glutathione, cysteine, cystine, cystamine and their glycosyl, N-acetyl, methyl, ethyl, propyl, amyl, butyl, and lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximines, buthionine sulfones, penta-, hexa-, heptathionine sulfoximine) in very low tolerated doses (e.g. pmol to $\mu$mol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, biliburin, biliverdin, EDTA and derivatives thereof, unsaturated fatty acids and derivatives thereof (e.g. γ-linolenic acid, linoleic acid, oleic acid), folic acid and derivatives thereof, ubiquinone and ubiquinole and derivatives thereof, vitamin C and derivatives thereof (e.g. ascorbyl palmitate, Mg ascorbyl phosphate, ascorbyl acetate), tocopherol and derivatives (e.g. vitamin E acetate, tocotrienol), vitamin A and derivatives (vitamin A palmitate), and coniferyl benzoate of benzoin resin, rutinic acid and derivatives thereof, α-glucosylrutin, ferulic acid, furfurylideneglucitol, carnosine, butylhydroxytoluene, butylhydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide).

The amount of abovementioned antioxidants (one or more compounds) in the preparations is preferably from 0.001 to 30% by weight, particularly preferably from 0.05 to 20% by weight, in particular from 1 to 10% by weight, based on the total weight of the preparation.

If vitamin E and/or derivatives thereof are the antioxidant (s), it is advantageous to choose their respective concentration from the range from 0.001 to 10% by weight, based on the total weight of the formulation.

If vitamin A and/or derivatives thereof or carotenoides are the antioxidant(s), it is advantageous to choose their respective concentration from the range from 0.001 to 10% by weight, based on the total weight of the formulation.

Customary oil components in cosmetics are, for example, paraffin oil, glyceryl stearate, isopropyl myristate, diisopropyl adipate, cetylstearyl 2-ethylhexanoate, hydrogenated polyisobutene, vaseline, caprylic/capric triglycerides, microcrystalline wax, lanoline and stearic acid.

The total content of auxiliaries and additives can be from 1 to 80% by weight, preferably from 6 to 40% by weight, and the nonaqueous content ("active substance") can be from 20 to 80% by weight, preferably from 30 to 70% by weight, based on the compositions. The compositions can be prepared in a manner known per se, i.e. for example by hot, cold, hot-hot/cold or PIT emulsification. This is a purely mechanical process; no chemical reaction takes place.

Sunscreen preparations of this type can, accordingly, be in liquid, paste or solid form, for example as water-in-oil creams, oil-in-water creams and lotions, aerosol foam creams, gels, oils, wax pencils, powders, sprays or alcoholic-aqueous lotions.

Finally, it is also possible to co-use other substances which absorb in the UV region and are known per se, as long as they are stable in the overall system of the combination of UV filters to be used according to the invention.

Most of the light protection agents in the cosmetic and pharmaceutical preparations used for protecting the human epidermis consist of compounds which absorb UV light in the UV-B region, i.e. in the range from 280 to 320 nm. For example, the proportion of the UV-A absorbers to be used according to the invention is from 10 to 90% by weight, preferably from 20 to 50% by weight, based on the total amount of UV-B- and UV-A-absorbing substances.

The UV filter substances used in combination with the compounds of the formula I to be used according to the invention are any UV-A and UV-B filter substances. Examples which may be mentioned are:

| No. | Substance | CAS No. (=acid) |
|---|---|---|
| 1 | 4-Aminobenzoic acid | 150-13-0 |
| 2 | 3-(4-Trimethylammonium)benzylidenbornan-2-one methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and its sodium salt | 4065-45-6 |
| 13 | 3-(4'-Sulfobenzylidene)bornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-Trianilino(o-carbo-2'-ethylhexyl-1'-oxy)-1,3,5-triazine | 88122-99-0 |
| 18 | 3-Imidazol-4-yl-acrylic acid and its ethyl ester | 104-98-3 |
| 19 | Ethyl 2-cyano-3,3-diphenylacrylate | 5232-99-5 |
| 20 | 2-Ethylhexyl 2-cyano-3,3-diphenylacrylate | 6197-30-4 |
| 21 | Menthyl-o-aminobenzoates (5-methyl-2-(1-methylethyl)-2-aminobenzoates) | 134-09-8 |
| 22 | Glyceryl p-aminobenzoate (1-glyceryl 4-aminobenzoate) | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (Mexonone) | 1641-17-4 |
| 25 | Triethanolamine salicylate | 2174-16-5 |
| 26 | Dimethoxyphenylglyoxalic acid (sodium 3,4-dimethoxyphenylglyoxalate) | 4732-70-1 |
| 27 | 3-(4-Sulfobenzylidene)bornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |
| 30 | 2,2'-Methylenebis[6(2H-benzotriazol-2-yl)-4-(1,1,3,3-tetramethylbutyl)phenol] | 103597-45-1 |
| 31 | 2,2'-(1,4-Phenylene)bis-1H-benzimidazole-4,6-disulfonic acid, Na salt | 180898-37-7 |
| 32 | 2,4-bis[4-(2-Ethylhexyloxy)-2-hydroxy]phenyl-6-(4-methoxyphenyl)-(1,3,5)-triazine | 187393-00-6 |

The cosmetic and dermatological preparations according to the invention can further advantageously comprise inorganic pigments based on metal oxides and/or other metal compounds which are insoluble or sparingly soluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides. Particular preference is given to pigments based on $TiO_2$ and ZnO.

For the purposes of the present invention, it is particularly advantageous, although not obligatory, for the inorganic pigments to be present in hydrophobic form, i.e. to have been surface-treated to repel water. This surface treatment can involve providing the pigments, in a manner known per se, as described in DE-A-33 14 742, with a thin hydrophobic layer.

To protect human hair from UV rays, the light protection agents of the formula I according to the invention can be incorporated into shampoos, lotions, gels, hairsprays, aerosol foam creams or emulsions in concentrations of from 0.1 to 10% by weight, preferably from 1 to 7% by weight. The particular formulations can be used, inter alia, for washing, coloring or for styling the hair.

The compounds to be used according to the invention usually have a particularly high absorbancy in the region of UV-A radiation with a sharp band structure. Furthermore, they are readily soluble in cosmetic oils and can be readily incorporated into cosmetic formulations. The emulsions prepared using the compounds to be used according to the invention are notable in particular for their high stability and the preparations produced using it have a pleasant feel on the skin.

The UV filter action of the compounds to be used according to the invention can also be utilized for stabilizing active ingredients and auxiliaries in cosmetic and pharmaceutical formulations.

The compounds according to the invention are highly suitable for stabilizing organic materials against the effect of light, oxygen and heat.

Examples of plastics which can be stabilized by the compounds I according to the invention which may be mentioned are:

polymers of mono- and diolefins, such as, for example, low or high density polyethylene, polypropylene, linear polybut-1-ene, polyisoprene, polybutadiene and copolymers of mono- or diolefins or mixtures of said polymers;

copolymers of mono- or diolefins with other vinyl monomers, such as, for example, ethylene-alkyl acrylate copolymers, ethylene-alkylmethacrylate copolymers, ethylene-vinylacetate copolymers or ethylene-acrylic acid copolymers;

polystyrene and copolymers of styrene or α-methylstyrene with dienes and/or acrylic derivatives, such as, for example, styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS) or methylmethacrylate-butadiene-styrene (MBS);

halogen-containing polymers, such as, for example, polyvinyl chloride, polyvinyl fluoride, polyvinylidene fluoride and copolymers thereof;

polymers derived from α, β-unsaturated acids and derivatives thereof, such as polyacrylates, polymethacrylates, polyacrylamides and polyacrylonitriles;

polymers derived from unsaturated alcohols and amines and from their acrylic derivatives or acetals, e.g. polyvinyl alcohol and polyvinyl acetate;

polyurethanes, polyamides, polyureas, polyphenylene ethers, polyesters, polycarbonates, polyoxymethylenes, polysulfones, polyether sulfones and polyether ketones.

The compounds I according to the invention can also be used to stabilize surface coatings, e.g. industrial coatings. Of these, particular emphasis is given to stoving finishes, and of these, in turn, automotive finishes, preferably two-coat finishes.

The compounds I according to the invention can be added to the coating in solid or dissolved form. In this context, their ready solubility in coating systems is of particular advantage.

Preference is given to using the compounds I according to the invention for stabilizing polyolefins, in particular polyethylene, polycarbonates, polyamides, polyesters, polystyrene, ABS and polyurethanes. In particular, it is also possible to stabilize films made of said plastics.

For these fields of use, the compounds are used in concentrations of from 0.01 to 5% by weight, based on the amount of plastic, preferably in a concentration of from 0.02 to 2% by weight. The combination with other stabilizers, for example antioxidants, metal deactivators or other light protection agents, and with antistatic or flame-inhibiting agents, is often advantageous. Particularly important costabilizers are, for example, sterically hindered phenols and phosphites, phosphonites, amines and sulfur compounds.
Examples of Suitable Costabilizers are:

phenolic antioxidants such as 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl) benzene, 1,3,5-tris(3,5-di-tert-butyl-4-hydroxybenzyl) isocyanurate, 1,3,5-tris[β-(3,5-di-tert-butyl-4-hydroxyphenyl)propionylethyl]isocyanurate, 1,3,5-tris(2,6-dimethyl-3-hydroxy-4-tert-butylbenzyl) isocyanurate and pentaerythritol tetrakis[β-(3,5-di-tert-butyl-4-hydroxy)propionate], phosphorus-containing antioxidants such as tris (nonylphenyl) phosphite, distearylpentaerythritol phosphite, tris(2,4-di-tert-butylphenyl) phosphite, tris (2-tert-butyl-4-methylphenyl) phosphite, bis(2,4-di-tert-butylphenyl) pentaerythritol diphosphite and tetrakis(2,4-di-tert-butylphenyl)-4,4'-biphenylenediphosphite, sulfur-containing antioxidants such as dilauryl thiodipropionate, dimyristyl thiodipropionate, distearyl thiodipropionate, pentaerythritol tetrakis(β-laurylthiopropionate) and pentaerythritol tetrakis(β-hexylthiopropionate), sterically hindered amines such as bis(2,2,6,6-tetramethylpiperidyl)sebacate, bis(1,2,2,6,6-pentamethylpiperidyl)sebacate, bis(1,2,2,6,6-pentamethylpiperidyl)ester, N,N'-bis(formyl)bis(2,2,6,6-tetramethyl-4-piperidyl)-1,6-hexane-diamine, the condensation product of 1-hydroxy-2,2,6,6-tetramethyl-4-hydroxypiperidine and succinic acid, the condensation product of N,N'-(2,2,6,6-tetramethylpiperidyl)hexamethylenediamine and 4-tert-octylamino-2,6-dichloro-1,3,5-s-triazine, poly [3-(eicosyl/tetracosyl)-1-(2,2,6,6-tetramethylpiperidin-4-yl)pyrrolidin-2,5-dione], tris(2,2,6,6-tetramethylpiperidyl)nitrilotriacetate, tetrakis(2,2,6,6-tetramethyl-4-piperidyl)-1,2,3,4-butanetetra-carboxylic acid, 1,1'-(1,2-ethanediyl)bis(3,3,5,5-tetramethylpiperazinone), the condensation products of 4-amino-2,2,6,6-tetramethylpiperidines and tetramethylolacetylenediureas, and 2-(2'-hydroxyphenyl)benzotriazoles, 2-hydroxybenzophenones, aryl esters of hydroxybenzoic acids, α-cyanocinnamic acid derivatives, nickel compounds or oxalic dianilides.

For mixing the compounds I according to the invention, especially with plastics, it is possible to use all known equipment and methods for incorporating stabilizing agents or other additives into polymers.

The examples below illustrate the preparation and use in more detail.

EXAMPLES

Example 1

20.5 g (0.1 mol) of methyl 2,2-bismethylmercapto-1-cyanoacrylate (prepared according to the details of CH 601984) and 12.5 g (0.1 mol) of 2-mercaptoaniline are stirred overnight in 100 ml of ethanol at room temperature. The precipitate which forms is filtered off with suction, washed with ethanol and acetone and dried at 200 mbar and 100° C. Yield: 20.2 g (87% of theory) of a white powder.

The absorption properties are listed in Table 1. Further Examples 2 to 23 as in Tables 1, 2 and 3 are obtained analogously. Substituents in the aromatic rings can also be introduced later.

For this, 5.8 g (250 mmol) of the compound of Example 1, for example, are dissolved in 50 ml of dimethylformamide, admixed with 4.1 g (250 mmol) of bromohexane and 3.45 g (250 mmol) of. potassium carbonate, and the mixture is boiled for 1 h with reflux condensation. 50 ml of water are then added, as result of which the product precipitates out. The resulting compound is Example 17, as can be seen from Table 2. The product is filtered off with suction, washed with water and dried at room temperature under reduced pressure (200 mbar). Yield: 5 g of a pale yellow powder (63% of theory).

TABLE 1

|  | $R^4$ | X | $R^2$ | $\lambda_{max}$ | $E^1_1$ |
|---|---|---|---|---|---|
| 1 | H | S | $COOCH_3$ | 336 | 1723 |
| 2 | H | NH | CN | 314 | 2297 |
| 3 | H | NH | $COOCH_3$ | 316 | 1986 |
| 4 | $OCH_3$ | NH | CN | 326 | 1784 |
| 5 | $OCH_3$ | NH | $COOCH_3$ | 328 | 1601 |
| 6 | $COOC_2H_5$ | NH | CN | 334 | 821 |
| 7 | $COOC_2H_5$ | NH | $COOCH_3$ | 332 | 952 |
| 8 | $CH_3$ | NH | CN | 318 | 2055 |
| 9 | $CH_3$ | NH | $COOCH_3$ | 320 | 1854 |
| 10 | H | O | CN | 308 | 1844 |
| 11 | H | O | $COOCH_3$ | 310 | 1778 |
| 12 | H | S | CN | 334 | 1776 |

TABLE 2

| | R³ | R⁵ | $\lambda_{max}$ | $E^1_1$ |
|---|---|---|---|---|
| 13 | CH₃ | 2-ethylhexyl | 340 | 1150 |
| 14 | CH₃ | (3,3,5-trimethylcyclohexyl methoxy) | 340 | 1090 |
| 15 | n-C₆H₁₃ | 2-ethylhexyl | 340 | 830 |
| 16 | n-C₆H₁₃ | (3,3,5-trimethylcyclohexyl methoxy) | 340 | 790 |
| 17 | n-C₆H₁₃ | CH₃ | 340 | 1200 |
| 18 | n-C₄H₉ | n-C₄H₉ | 340 | 1250 |

The compound of Example 18 was obtained as follows:

0.1 mol of mercaptoaniline and 0.1 mol of butyl 2,2-bismercapto-1-cyanoacrylate were heated to 80° C. in 100 ml of ethanol. The mixture was then cooled to 0° C., and the precipitated product was filtered off with suction. Washing with acetic ester and drying at 200 mbar and 60° C. gave 20.5 g of white crystals (75% of theory).

A mixture of 0.1 mol of the reaction product, 0.1 mol of potassium carbonate and 0.11 mol of butyl bromide in 100 ml of dimethylformamide were stirred at 100° C. for 6 hours. The mixture was then cooled to room temperature, and the precipitated salt was filtered off with suction. The filtrate was diluted with 200 ml of water and extracted with three× 100 ml of dichloromethane. The organic phases were combined, dried over sodium sulfate and concentrated by evaporation. The resulting yellow oil was chromatographed on silica gel with 4:1 cyclohexane/acetic ester. From the second fraction, 6 g (i.e. 18% of theory) of compound 18 were isolated as slightly yellow crystals.

TABLE 3

| | Formula | $\lambda_{max}$ | $E^1_1$ |
|---|---|---|---|
| 19 | (benzoxazole-SO₃H, cyanoacrylate-OR) | 312 | 1125 |
| 20 | (benzothiazole-N-propyl-SO₃H, cyano-ester-OCH₃) | 340 | 1200 |
| 21 | (benzoyl-benzimidazole, cyano-ester-O-methyl) | 348 | 740 |
| 22 | (benzimidazole-N,N-diC₆H₁₃, cyano-ester-OCH₃) | 325 | 970 |
| 23 | (benzothiazole-N-CH₃, cyano-ester-O-ethyl-SO₃H) | 340 | 1160 |
| 24 | (perimidine, NC-cyano-ester-OCH₃) | 296 | 1503 |

APPLICATION EXAMPLES

Example 25

Standard Method for Determining Photostability (Sun Test)

A 5% strength by weight alcoholic solution of the light protection agent to be tested is applied, using an Eppendorf pipette (20 μl), to the milled area of a small glass plate. Owing to the presence of the alcohol, the solution distributes uniformly on the roughened surface of the glass. The amount applied corresponds to the amount of light protection agent required to achieve an average sun protection factor in suncreams. In the test, four small glass plates are irradiated in each case. The evaporation time and the irradiation each last for 30 minutes. The small glass plates are cooled slightly during irradiation using a water cooling system located at the base of the sun test apparatus. The temperature inside the sun test apparatus is 40° C. during irradiation. After the samples have been irradiated, they are washed with ethanol in a dark 50 ml graduated flask and measured using a photometer. The blank samples are likewise applied to small glass plates and evaporated at room temperature for 30 minutes. Like the other samples, they are washed off with ethanol and diluted to 100 ml and measured.

General Procedure for the Preparation of Emulsions for Cosmetic Purposes

All of the oil-soluble constituents are heated to 85° C. in a stirred vessel. When all of the constituents are molten or are in the form of a liquid phase, the aqueous phase is incorporated with homogenization. While being stirred, the emulsion is cooled to about 40° C., perfumed and homogenized and then cooled to 25° C. with continuous stirring.

Preparations

Example 26

| Lipcare composition Mass content (% by weight) | |
|---|---|
| ad 100 | Eucerinum anhydricum |
| 10.00 | glycerol |
| 10.00 | titanium dioxide, micronized |
| 5.00 | compound No. 18 in Table 2 |
| 8.00 | octyl methoxycinnamate |
| 5.00 | zinc oxide |
| 4.00 | castor oil |
| 4.00 | pentaerythritol stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

Example 27

| Sunblock composition containing micropigments Mass content (% by weight) | |
|---|---|
| ad 100 | water |
| 10.00 | octyl methoxycinnamate |
| 6.00 | PEG-7 hydrogenated castor oil |
| 6.00 | titanium dioxide, micronized |
| 5.00 | compound No. 18 in Table 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

Example 28

| Grease-free gel Mass content (% by weight) | |
|---|---|
| ad 100 | water |
| 8.00 | octyl methoxycinnamate |
| 7.00 | titanium dioxide, micronized |
| 5.00 | compound No. 18 in Table 2 |
| 5.00 | glycerol |
| 5.00 | PEG-25 PABA |
| 1.00 | 4-methylbenzylidenecamphor |
| 0.40 | acrylate C10—C30—alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

Example 29

| Suncream (SPF 20) Mass content (% by weight) | |
|---|---|
| ad 100 | water |
| 8.00 | octyl methoxycinnamate |
| 8.00 | titanium dioxide, micronized |
| 6.00 | PEG-7 hydrogenated castor oil |
| 5.00 | compound No. 18 in Table 2 |
| 6.00 | mineral oil |
| 5.00 | zinc oxide |
| 5.00 | isopropyl palmitate |
| 0.30 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

Example 30

| Water-resistant suncream Mass content (% by weight) | |
|---|---|
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | compound No. 18 in Table 2 |
| 4.00 | glycerol |
| 3.00 | jojoba oil |
| 2.00 | 4-methylbenzylidenecamphor |
| 2.00 | titanium dioxide, micronized |
| 1.50 | PEG-45/dodecyl glycol copolymer |
| 1.50 | dimethicone |
| 0.70 | magnesium sulfate |
| 0.50 | magnesium stearate |
| 0.15 | fragrance |

Example 31

| Sunmilk (SPF 6) Mass content (% by weight) | |
|---|---|
| ad 100 | water |
| 10.00 | mineral oil |
| 6.00 | PEG-7 hydrogenated castor oil |
| 5.00 | isopropyl palmitate |
| 3.50 | octyl methoxycinnamate |
| 5.00 | compound No. 18 in Table 2 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 3.00 | glycerol |
| 0.25 | methylparaben |
| 0.15 | propylparaben |
| 0.05 | tocopherol |

We claim:

1. A method for treating human skin and/or human hair against solar rays which comprises applying thereto, as a photostable UV filter in a cosmetic and/or pharmaceutical preparation, a composition comprising at least one compound of the formula I

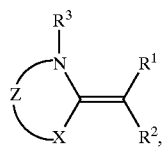

in which $R^1$ and $R^2$ are identical or different, electron-withdrawing radicals chosen from the group consisting of cyano, alkyl- or arylcarbonyl, alkyloxy- or aryloxycarbonyl and optionally substituted aminocarbonyl, $R^3$ is a hydrogen atom, a $C_1$–$C_{20}$-alkyl radical or a $C_3$–$C_{20}$-cycloalkyl radical or a radical of the formula —$CH_2$—$CH_2$—$SO_3$—$M^+$, where $M^+$ is a cation, X is the divalent radical of oxygen, sulfur or the radical

where $R^3$ is as defined above,

Z is the divalent radical of the formula II or III, which forms a fused system with the radical of the formula I

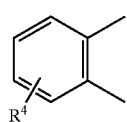

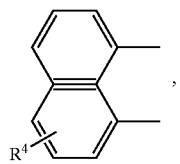

where $R^4$ can be bonded one or more times to the benzylidene ring I or naphthylidene ring II, and is hydrogen, alkyl, cycloalkyl, alkyloxy, cycloalkyloxy, alkoxycarbonyl, mono- or dialkylaminocarbonyl, alkylamino, dialkylamino, each having up to 20 carbon atoms, and also cyano, amino and $SO_3$—$M^+$, where $M^+$ is a cation.

2. The method of claim 1, wherein $R^1$ is cyano or alkyloxycarbonyl having from 2 to 12 carbon atoms, $R^2$ is hydrogen, $R^3$ is hydrogen or methyl, and $R^4$ is $C_1$–$C_8$-alkyl, $C_1$–$C_8$-alkoxy or $SO_3$—$M^+$, where $M^+$ is a cation chosen from the group consisting of $H^+$, optionally substituted ammonium, and metal cations.

3. A cosmetic preparation comprising light protection agents, for protecting the human epidermis or human hair from UV light in the range from 280 to 400 nm, which comprises, in a cosmetically suitable carrier, alone or together with compounds which absorb in the UV region and are known per se for cosmetic and pharmaceutical preparations, compounds of the formula I

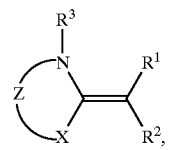

in which $R^1$ and $R^2$ are identical or different, electron-withdrawing radicals chosen from the group consisting of cyano, alkyl- or arylcarbonyl, alkyloxy- or aryloxycarbonyl and optionally substituted aminocarbonyl, $R^3$ is a hydrogen atom, a $C_1$–$C_{20}$-alkyl radical or a $C_3$–$C_{20}$-cycloalkyl radical or a radical of the formula —$CH_2$—$CH_2$—$SO_3$—$M^+$, where $M^+$ is a metal cation, X is the divalent radical of oxygen, sulfur or the radical

where $R^3$ is as defined above,

Z is the divalent radical of the formula II or III, which forms a fused system with the radical of the formula I

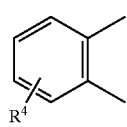

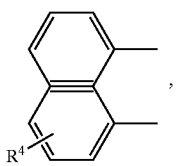

where R⁴ can be bonded one or more times to the benzylidene ring I or naphthylidene ring II, and is hydrogen, alkyl, cycloalkyl, alkyloxy, cycloalkyloxy, alkoxycarbonyl, mono- or dialkylaminocarbonyl, alkylamino, dialkylamino, each having up to 20 carbon atoms, and also cyano, amino and $SO_3-M^+$, where $M^+$ is a metal cation.

4. A cosmetic preparation comprising light protection agents as claimed in claim 3, which comprises compounds of the formula I in which Z is the radical of the formula II.

5. A cosmetic preparation comprising light protection agents as claimed in claim 3, which comprises compounds of the formula I in which $R^1$ is cyano or alkyloxycarbonyl having from 2 to 12 carbon atoms, $R^2$ is hydrogen, $R^3$ is hydrogen or methyl, and $R^4$ is $C_1-C_8$-alkyl, $C_1-C_8$-alkoxy or $SO_3-M^+$, where $M^+$ is a cation.

6. The method of claim 1 wherein Z is the radical of the formula II.

7. A plastic which includes, as a light protection agent for stabilizing the plastic, at least one compound of the formula I

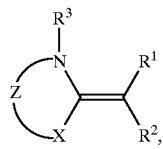

in which

R¹ and R² are identical or different, electron-withdrawing radicals chosen from the group consisting of cyano, alkyl- or arylcarbonyl, alkyloxy- or aryloxycarbonyl and optionally substituted aminocarbonyl, $R^3$ is a hydrogen atom, a $C_1-C_{20}$-alkyl radical or a $C_3-C_{20}$-cycloalkyl radical or a radical of the formula $-CH_2-CH_2-SO_3-M^+$, where $M^+$ is a cation, X is the divalent radical of oxygen, sulfur or the radical

where $R^3$ is as defined above,

Z is the divalent radical of the formula II or III, which forms a fused system with the radical of the formula I

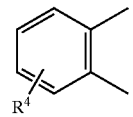

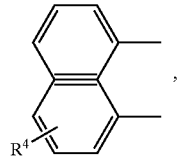

where R⁴ can be bonded one or more times to the benzylidene ring I or naphthylidene ring II, and is hydrogen, alkyl, cycloalkyl, alkyloxy, cycloalkyloxy, alkoxycarbonyl, mono- or dialkylaminocarbonyl, alkylamino, dialkylamino, each having up to 20 carbon atoms, and also cyano, amino and $SO_3-M^+$, where $M^+$ is a cation.

8. The method of claim 1 wherein in addition to compound I, at least one further compound which absorb in the UV region is included.

* * * * *